United States Patent [19]

Asche et al.

[11] Patent Number: 4,917,886

[45] Date of Patent: Apr. 17, 1990

[54] NOVEL TOPICALLY ADMINISTRABLE PHARMACEUTICAL COMPOSITIONS

[75] Inventors: Henning Asche, Bettingen; Heidi Affolter, Birsfelden, both of Switzerland

[73] Assignee: Ciba-Geigy Corporation, Ardsley, N.Y.

[21] Appl. No.: 396,781

[22] Filed: Aug. 21, 1989

Related U.S. Application Data

[63] Continuation of Ser. No. 193,188, May 10, 1988, abandoned, which is a continuation of Ser. No. 766,669, Aug. 15, 1985, abandoned, which is a continuation of Ser. No. 536,584, Sep. 28, 1983, abandoned.

[30] Foreign Application Priority Data

Oct. 7, 1982 [CH] Switzerland .................. 5898/82

[51] Int. Cl.$^4$ ............................................. A61K 31/78
[52] U.S. Cl. ..................................................... 424/81
[58] Field of Search ........................................... 424/81

[56] References Cited

U.S. PATENT DOCUMENTS

| | | | |
|---|---|---|---|
| 3,629,412 | 12/1971 | Silber et al. | 424/232 |
| 3,749,773 | 7/1973 | Ninger | 424/81 |
| 4,309,414 | 1/1982 | Inagi et al. | 424/273 |
| 4,390,532 | 6/1983 | Stuttgen et al. | 424/240 |
| 4,525,347 | 6/1985 | Inagi et al. | 424/81 |
| 4,551,475 | 3/1985 | Eckert | 514/408 |
| 4,807,824 | 1/1983 | Eckert | 514/408 |

FOREIGN PATENT DOCUMENTS

| | | |
|---|---|---|
| 0043738 | 1/1982 | European Pat. Off. . |
| 054205 | 6/1982 | European Pat. Off. . |
| 0104037 | 2/1983 | European Pat. Off. . |
| 2843901 | 4/1980 | Fed. Rep. of Germany . |
| 2827018 | 11/1980 | Fed. Rep. of Germany . |
| 47-5827 | 4/1972 | Japan . |
| 5651410 | 1/1979 | Japan . |
| 57-126414 | 1/1981 | Japan . |
| 979909 | 1/1965 | United Kingdom . |
| 1261881 | 1/1972 | United Kingdom . |
| 1356214 | 6/1974 | United Kingdom . |
| 1544351 | 4/1977 | United Kingdom . |
| 1476717 | 6/1977 | United Kingdom . |
| 2017491 | 10/1979 | United Kingdom . |
| 2023000 | 12/1979 | United Kingdom . |
| 1569424 | 6/1980 | United Kingdom . |
| 1594628 | 8/1981 | United Kingdom . |
| 2075837 | 11/1981 | United Kingdom . |
| 2098865 | 12/1982 | United Kingdom . |

OTHER PUBLICATIONS

American Heritage Dictionary-New College Edition, (1976), pp. 262, 429 and 547.
Eric W. Martin, Dispensing of Medication, 7th Edition, (1971), pp. 533 & 534.
PCT WO81/02673.
PCT/WO81/00206.
Chem. Abstr. 95:103322x (5/81), p. 357.
Patent Abstract of Japan, vol. 5, No. 111 (C-63) [783], 1981,

*Primary Examiner*—Stanley J. Friedman
*Attorney, Agent, or Firm*—JoAnn Villamizar

[57] ABSTRACT

Novel topically administrable pharamceutical composition containing, as active ingredient, from approximately 0.1 to approximately 10% by weight of a non-steroidal, anti-inflammatorily active compound having at least one acidic group, from approximately 10 to approximately 50% by weight of a water-soluble, volatile lower alkanol having from 2 up to and including 4 carbon atoms, from approximately 3 to approximately 15% by weight of an optionally self-emulsifying lipid or a mixture of lipids, from approximately 0.5 to approximately 2% by weight of a gel structure former, from approximately 1 to approximately 20% by weight of a co-solvent, from approximately 40 to approximately 80% by weight of water, optionally from approximately 0.5 to approximately 5% by weight of an emulsifier if the lipid phase is not self-emulsifying and, if desired, non-essential constituents.

21 Claims, No Drawings

NOVEL TOPICALLY ADMINISTRABLE PHARMACEUTICAL COMPOSITIONS

The therapeutic use of topically administrable pharmaceutical preparations is frequently indicated in those cases where oral or another form of parenteral administration leads to intolerability, risks or harmful side effects or where an undesired biotransformation of the active ingredient occurs. Application to the skin may, therefore, be advantageous if, for example, there is to be a continuous release of the active ingredient component, active ingredients are intended to act locally or act systemically with the gastro-intestinal tract being bypassed, or if active ingredients having a short biological half-life are to be used. A group of active ingredients suitable for topical administration is, for example, the non-steroidal, anti-inflammatory agents.

The possibilities of using customary topically administrable pharmaceutical preparations are limited, for example, by inadequate solubility of the active ingredient or by the inability of such formulations to channel the active ingredient through the skin barrier and thereby enable a systemic action.

Of the various kinds of medicinal formulations that are applied to the skin there may be mentioned, for example, suspensions, solutions, foams and emulsions, such as water/oil (W/O) and oil/water (O/W) emulsions, and also gels.

Hitherto unknown are dermatics that are to be regarded at the same time as O/W emulsion and as gel.

The present invention relates to the provision of a novel, almost neutral pharmaceutical preparation based on an oil/water emulsion and containing, as active ingredient, a non-steroidal, anti-inflammatorily active compound having at least one acidic group for topical use on intact epidermis, which preparation combines within it the properties of a gel with those of an oil/water emulsion, effects readier solubility of the active ingredient and which, if desired, is capable of transporting the active ingredient through the barrier of the stratum corneum, and to the use thereof and to the process for the manufacture of such formulations.

The novel, almost neutral topically administrable pharmaceutical composition has a pH of from approximately 5 to approximately 7.5 and contains from approximately 10 to approximately 50% by weight of a water-soluble, volatile lower alkanol having from 2 up to and including 4 carbon atoms, from approximately 1 to approximately 20% by weight of a co-solvent, from approximately 40 to approximately 80% by weight of water, from approximately 3 to approximately 15% by weight of an optionally self-emulsifying lipid or a mixture of lipids, optionally from approximately 0.5 to approximately 5% by weight of an emulsifier if the lipid phase is not self-emulsifying, from approximately 0.5 to approximately 2% by weight of a gel structure former, as active ingredient from approximately 0.1 to approximately 10% by weight of a non-steroidal, anti-inflammatorily active compound having at least one acidic group and, if desired, non-essential constituents.

The base substance according to the invention does not have the disadvantages described above. The advantages of this novel formulation reside, for example, in the favourable cosmetic properties, in a distinctly readier solubility of active ingredients and the associated higher effective active ingredient concentration and also in a considerably improved chemical stability of the active ingredient in comparison with conventional topical formulations.

As compared with a corresponding gel, the composition according to the invention is distinguished above all by the fact that the presence of the lipid phase and its fat-restoring properties enable the formulation to be massaged in whilst, at the same time, the direct absorption into the skin is experienced as a pleasant property. In addition, in comparison with hydrogels, there is an increased solubility for lipophilic active ingredients.

The advantages over an O/W emulsion reside in the enhanced cooling effect which is brought about by the coldness due to evaporation of the additional alcohol component. In addition, as compared with O/W emulsions, there is an improved solubility of polar medicinal active ingredients.

The interplay of alcohol component and co-solvent makes it possible to incorporate into a water-containing system, for example substances that are primarily sparingly soluble in water. For example, it is possible, by virtue of the fat component, successfully to incorporate lipophilic active substances into an aqueous system.

In addition, the alcohol and co-solvent component promotes improved resorbability of an active ingredient, compared with gels and O/W emulsions.

It is highly surprising that, for the first time, the manufacture of such a pharmaceutical preparation in a stable form has been successful although, according to the principles of general experience, the mixing of water-insoluble lower alkanols in the disclosed concentration with oil/water emulsions should result in their breakdown. As a result of the partial dissolution of the emulsifiers, a weakening of the emulsifier film stabilising the emulsion is what was to be expected.

The invention is further based on the surprising discovery that besides the galenical base substance, also the particular active ingredient in the composition according to the invention is in stable form. For example, extensive investigations of stability have shown that the active ingredient proves to be extremely stable towards chemical reactions with the base substance of the formulation. Equally, after relatively long storage, almost no degradation products of the active ingredient are detected although it is known, for example, of many non-steroidal anti-inflammatorily active acids that these are subjected, for example in a cream base substance, to chemical changes, such as reduction or esterification as a result of which a certain portion of the active ingredient is chemically modified and hence the active ingredient concentration is reduced in an undesirable manner. These phenomena could not be observed in the composition on which the invention is based, as is demonstrated by reference to the following stability comparison of a cream with a formulation according to the invention having the composition given below:

| (A) cream composition | | (B) composition according to the invention | |
|---|---|---|---|
| diclofenac-sodium | 1% | diclofenac-sodium | 1.0% |
| polyethylene glycol 300 | 7% | isopropanol | 20.0% |
| | | diethanolamine | 1.2% |
| glycerine stearate | 10% | acrylic acid polymerisate (Carbopol 934 P) | 1.0% |
| cetyl alcohol | 1% | | |
| isopropyl myristate | 5% | sodium sulphite | 0.1% |
| petroleum jelly, white, | 10% | polyhydroxyethylene cetyl stearyl ether (Cetomacrogol 1000) | 2.0% |
| polyhydroxyethylene (100)-stearate (Myrj 59) | 4% | paraffin oil, viscous | 2.5% |
| 2-phenoxyethanol | 1% | caprylic/capric acid | 2.5% |

| (A) cream composition | (B) composition according to the invention | |
|---|---|---|
| -continued | | |
| water, demineralised | 61% ester (Cetiol LC) | |
| | polyethylene glycol 300 | 3.0% |
| | water, demineralised | 66.7% |

After each formulation had been stored for 6 months at 35° C., chromatographic analysis, for example, showed for formulation A a content of approximately from 2 to 4% by weight of cetyl ester with the active ingredient and approximately from 2 to 4% by weight of reduction product, for example aldehyde and alcohol, formed from the active ingredient, whereas in formulation B according to the invention, despite the high proportion of lower alkanol, no esterification or reduction products of the active ingredient could be detected. This is highly surprising since, from a chemical standpoint, ester formation with a lower alkanol is favoured over esterification with a fatty alcohol (cetyl alcohol in this case).

Accordingly, the present invention relates also to a process for the stabilisation of non-steroidal, anti-inflammatorily active compounds having at least one acidic group in pharmaceutical compositions for topical administration, characterised in that there is added to a suitable galenical base substance from approximately 10 to approximately 50% by weight of a water-soluble, volatile lower alkanol having from 2 up to and including 4 carbon atoms.

The pharmaceutical compositions according to the invention can furthermore be used in a method for the treatment of painful conditions, inflammation and/or rheumatic diseases in warm-blooded animals. Corresponding formulations can be applied, for example, 2 or 3 times daily to the intact epidermis. When this novel pharmaceutical formulation is administered topically, the particular medicinal active ingredient can penetrate transcutaneously, in particular overcoming the skin barrier of the epidermis, for example into the corium or the subcutis and be taken up by the vascular system (resorption).

In the case of an intact epidermis, the interface between the dead stratum corneum and the stratum granulosum represents the main obstacle to the penetration of active ingredient molecules into the region of the corium and the subcutis through which pass blood and lymph systems.

The reason for the favourable resorption properties of the composition according to the invention lies, on the one hand, in the alteration of the stratum corneum structure which is contingent on the alcohol content, whereby, at the same time, the barrier function of the stratum corneum is to some extent removed and, on the other hand, in the carrier function of the co-solvent and finally in the readier solubility of the medicinal active ingredient.

The alcohol component used in the composition according to the invention includes especially lower alkanols having preferably 2 or 3 carbon atoms, such as ethanol or especially isopropanol, and also mixtures thereof. The preferred alcohol proportion in the formulation according to the invention is at least 15% by weight, especially from approximately 20 to approximately 30% by weight.

The function of the co-solvent is to maintain the active ingredient left behind on the skin in solution. In addition, the co-solvent must be miscible with the aqueous-alcoholic phase. Suitable for this purpose are, for example, polyhydric alcohols, such as glycerine, ethylene glycol or propylene glycol, especially poly-lower alkylene glycols, for example polyethylene glycol or polypropylene glycol, having a chain length of from approximately 200 to approximately 6000, preferably from approximately 300 to approximately 1500, units. Preferably, from approximately 5 to approximately 10% by weight are co-solvent.

The fatty phase constituents (lipids) that can be used for the novel formulation can be divided into those having non-emulsifying properties and those having self-emulsifying properties. The lipids can be of a vegetable or animal nature and also partly or completely synthetic. Accordingly, there come into consideration as fatty phase constituents, for example, lipids without ester linkages, such as hydrocarbons, fatty alcohols, sterols, fatty acids and salts thereof, and lipids having ester linkages, such as glycerides, waxes and phosphatides. The hydrocarbons include, for example, liquid, semi-solid or solid substances and mixtures, such as paraffins, petroleum jelly, solid paraffin and microcrystalline wax. Fatty alcohols can have, for example, 1 or 2 hydroxy functions and a carbon atom number of approximately from 6 to 34 and be saturated or unsaturated. Those having an even number of carbon atoms, especially those having from 12 to 18 carbon atoms, are preferred. Primary, linear and saturated fatty alcohols are, for example, decanol (capric alcohol), dodecanol (lauryl alcohol), tetradecanol (myristyl alcohol), hexadecanol (cetyl alcohol), octadecanol (stearyl alcohol), eicosanol (arachidyl alcohol), docosanol (behenyl alcohol). The 2-alkyl-fatty alcohols include, for example, 2-hexyl-decanol or 2-octyl-dodecanol. Examples of α-alkanediols that may be mentioned are, for example, 1,12-octadecanediol or 9c-octadecen-1-ol.

Sterols are, for example, naturally occurring steroids that have a 3β-hydroxy group and an aliphatic side chain in the 17β-position and are derived, for example, from parent hydrocarbon cholestane, ergostane and stigmastane, such as cholesterol and lanolin.

Fatty acids can be saturated or unsaturated and have, for example, from 6 to 24 carbon atoms, 10 to 18 carbon atoms and an even number of carbon atoms being preferred. Examples of saturated fatty acids are: hexanoic acid (caproic acid), octanoic acid (caprylic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), docosanoic acid (behenic acid). Stearic acid is especially preferred. Mono-unsaturated fatty acids are, for example: 9-dodecenoic acid (lauroleic acid), 9-tetradecenoic acid (myristoleic acid), 9-hexadecenoic acid (palmitoleic acid), 9-octadecenoic acid (oleic acid), 6-octadecenoic acid (petroselic acid), 9-eicosanoic acid (gadoleic acid), 13-docosenoic acid (erucic acid), whilst as polyunsaturated fatty acids there are suitable, for example, 9,12-octadecadienoic acid (linoleic acid) and 9,12,15-octadecatrienoic acid (linolenic acid). As salts of such fatty acids there come into consideration, for example, alkali metal salts, such as sodium or potassium salts, ammonium salts or amine salts, such as mono-, di- or tri-substituted amines, for example corresponding lower alkylamines or lower alkanolamines, for example corresponding mono-, di- or tri-ethylamines or -ethanolamines.

Glycerides are understood to mean fatty acid esters of glycerine, it being possible for various fatty acid constituents, for example those mentioned above, to occur within the glyceride. In the case of an increased content of unsaturated fatty acids, the corresponding glycerides are liquid (oils). Glycerides and oils are, for example, groundnut oil (arachis oil), olive oil, castor oil, sesame oil, it being possible also for the oils to be hydrogenated, such as hydrogenated groundnut oil, hydrogenated cotton seed oil, for example Sterotex ®, hydrogenated castor oil, for example Cutina ®HR. As semi-synthetic and completely synthetic glycerides there come into consideration, for example, caprylic/capric acid triglyceride, for example Miglyol ®812 or Syndermin ®GTC, or mono-, di- or tri-esters of palmitic and stearic acid, for example Precirol ®.

Waxes are likewise defined as fatty acid esters but, instead of glycerine, there are suitable as alcohol components alcohols of the sterine series and lower alcohols, for example having from 1 up to and including 12 carbon atoms, such as ethanol, isopropanol or decanol, and also higher even-numbered aliphatic alcohols, for example having from 16 to 36 carbon atoms, especially those mentioned above. Solid and semi-synthetic waxes are, for example, beeswax, carnauba wax, cetyl palmitate, for example Cutina ®CP, wool wax, and lanolin, and liquid waxes are, for example, isopropyl myristate, isopropyl stearate, oleic acid decyl ester, for example Cetiol ®V, ethyl oleate, caprylic/capric acid esters of saturated fatty alcohols, especially having from 12 to 18 carbon atoms, for example Cetiol ®LC.

As phosphatides there come into consideration especially phosphoglycerides, preferably phosphatidyl cholines which are produced by esterification of sn-glycerine-3-phosphoric acid with a saturated and an unsaturated fatty acid, the phosphoric acid residue being for its part esterified by choline (also called lecithins). For example, egg lecithin or soya lecithin are used.

If, for example, the fatty alcohol is etherified, for example by a lower alkanol or a lower alkoxy-lower alkanol, such as ethanol, a propanol, ethoxyethanol, a methoxy- or ethoxy-propanol, the fatty alcohol may be self-emulsifying, such as ethoxylated fatty alcohols, for example polyhydroxyethylene cetyl stearyl ether, such as Cetomacrogol1000 ®.

The fat constituent of the composition according to the invention is preferably from approximately 5 to approximately 10% by weight and can also include mixtures of the compounds mentioned above.

A further constituent of the pharmaceutical preparation according to the invention is emulsifiers the surface-active character of which is determined by the spatially separate lipophilic and hydrophilic centres in the same molecule. Preferably, anion-active surfactants having an acidic hydrophilic group and non-ionogenic surfactants are used.

Corresponding anionic emulsifiers are especially carboxylates, such as readily or sparingly soluble fatty acid salts, salts of fluorinated fatty acids, of alkoxy-carboxylic acids, of sulphonamidocarboxylic acids, of fatty acid lactates, of alkylmalonic or alkylsuccinic acids, sulphonates, for example readily or sparingly soluble alkyl sulphonates, sulphonated fatty acid alkyl esters, fatty acid sulphonates, fatty acid ester sulphonates, perfluorinated alkyl sulphonates, readily or sparingly soluble alkylbenzene sulphonates, and sulphates, for example sulphated primary or secondary fatty alcohols, soaps, esters, amides, alkanolamides, mono- or poly-glycerides, polyglycol ethers, for example of fatty alcohols and alkylphenols. Of the great number of suitable anionic emulsifiers there may be mentioned: soluble soaps, such as sodium palmitate, stearate, oleate and triethanolammonium stearate, alkali metal salts, such as sodium salts, of fatty alcohol sulphates, for example sodium lauryl sulphate or sodium cetyl stearyl sulphate, and sulphosuccinates, such as sodium dioctyl sulphosuccinate.

Non-ionic emulsifiers are, for example, fatty acid esters with mono- or poly-hydric alcohols, such as lower alkanols, ethylene glycol, propylene glycol, with oligohydroxy compounds, such as sorbitol, pentaerythritol or saccharose, or with polyhydroxy compounds, such as polyethylene glycol or polypropylene glycol. Especially suitable are partial glycerine fatty acid esters, glycerine monostearate, partial fatty acid esters of sorbitan, such as sorbitan monolaurate, stearate or sesquioleate, partial fatty acid esters of polyhydroxyethylene sorbitan, especially having from approximately 5 to approximately 20 oxyethylene units, such as polyethylene glycol (20)-sorbitan monostearate or monooleate. Other likewise preferred non-ionic emulsifiers are, for example, polyethylene and polypropylene glycol ethers, especially having approximately from 2 to 23 ethylene glycol or ethylene oxide units, of alcohols, such as fatty alcohols, for example of the kind mentioned above, and also polyethers, of fatty acid esters, equally of the etherified and those of the glycerine and sorbitan type, or of fatty amines, such as the corresponding fatty amines derived from the fatty alcohols. Examples of such non-ionic emulsifiers that may be mentioned are: polyhydroxyethylene fatty alcohol ethers, especially having from approximately 12 to approximately 30 mole equivalents of oxyethylene, such as polyhydroxyethylene cetyl stearyl ether, for example Cetomacrogol 1000, polyhydroxyethylene (4)-lauryl ether, polyhydroxyethylene (23)-lauryl ether and others, polyhydroxyethylene fatty acid esters, such as polyhydroxyethylene stearates, especially having from 8 to 1000 oxyethylene groups, for example Myrj 59, and also polyhydroxyethylene glycerine fatty acid esters, for example Tagat S. Also suitable are ethylene oxide and propylene oxide block copolymers having hydrophilic polyhydroxyethylene groups and hydrophobic polyhydroxypropylene groups, for example polyoxyethylenepolyoxypropylene polymers, especially having a molecular weight of from approximately 1000 to approximately 11000, for example Pluronic ®F 68. Preferred pharmaceutical formulations contain from approximately one to approximately two per cent by weight of emulsifier.

As gel structure formers in the matrix of which is stored the water necessary for the formulation there are used inorganic and organic macromolecules. The base for high molecular weight inorganic components with gel-forming properties is predominantly water-containing silicates, such as aluminium silicate or magnesium aluminium silicates, such as Veegum, or colloidal silica, such as Aerosil. As high molecular weight organic substances there are used, for example, natural, semi-synthetic or synthetic macromolecules. Natural and semi-synthetic polymers are derived, for example, from polysaccharides having the most varied carbohydrate units, such as celluloses, starches, tragacanth, agar-agar, alginic acid and salts thereof, for example sodium alginate, and derivatives thereof, such as lower alkyl celluloses, for example methyl or ethyl celluloses, carboxyor hydroxy-lower alkyl celluloses, such as carboxymethyl, hydroxyethyl, hydroxypropyl, hydroxypropylmethyl and ethylhydroxyethyl celluloses. Natural and semi-synthetic polymers include, for example, gelatine and gum arabic. The units of synthetic gel-forming macromolecules are, for example, vinyl alcohols, vinyl pyrrolidine, acrylic or methacrylic acid, and as examples of such polymers there may be mentioned polyvinyl alcohol derivatives, especially having a molecular weight of from approximately 28000 to approximately 40000, such as Polyviol® or Moviol®, polyvinyl pyrrolidines, especially having a molecular weight of from approximately 10000 to approximately 1 million, such as Kollidon® or Plasdone®, polyacrylates and polymethacrylates, especially having a molecular weight of from approximately 80000 to approximately 1 million, or salts thereof, such as Rohagit S®, Eudispert® or Carbopol®. The preferred per cent by weight range when using a gel structure former or a mixture thereof is from approximately 1 to approximately 1.5 per cent by weight.

As preferred categories of active ingredient there come into consideration especially those for systemic treatment that are to be applied to the intact skin, are to enter the skin layers, penetrate these and primarily pass into the circulation of the vascular system of the corium and the subcutis and possibly of the subcutaneous tissue lying beneath the latter and also of the muscle region.

There come into consideration as non-steroidal, anti-inflammatorily active compounds having at least one acidic group for systemic treatment, for example, salicylic acid and derivatives thereof, such as diflunisal, flufenamic acid or tolfenamic acid, ketoalkanecarboxylic acids and derivatives thereof, such as fenbufen, aryl- and heteroaryl-alkylcarboxylic acids, such as phenylalkanecarboxylic acids and derivatives thereof, for example diclofenac, ketoprofen, pirprofen, fluoprofen, flurbiprofen, ibuprofen, suprofen, miprofen, and pyrrole-lower alkanecarboxylic acids and derivatives thereof, for example zomepirac, tolmetin or clopirac, lower alkanecarboxylic acids having di- or tri-cyclic aryl and heteroaryl groups, such as naproxen, sulindac, indomethacin, carprofen or pranoprofen, also pyrazole compounds, such as pyrazolealkanecarboxylic acids, such as lonazolac or pirazolac, or salts thereof. Especially preferred representatives are, for example, diclofenac and pirprofen and salts thereof. The preferred proportion of active ingredient is, for example, from approximately 1 to approximately 5% by weight. Salts of active ingredients having acidic groups, such as carboxyl groups, are derived primarily from bases. Corresponding salts are, for example, metal salts, such as alkali metal or alkaline earth metal salts, for example sodium, potassium, magnesium or calcium salts, aluminium salts or transition metal salts, such as zinc or copper salts, or corresponding salts with ammonia or organic amines. Organic amines that come into consideration are, for example, the following: alkylamines, such as mono-, di- or tri-lower alkylamines, alkylenediamines, such as lower alkylenediamines, alkylamines substituted by phenyl, such as mono- or di-phenyl-lower alkylamines, hydroxyalkylamines, such as mono-, di- or tri-hydroxy-lower alkylamines, an oligohydroxy-lower alkylamine or hydroxy-lower alkyl-di-lower alkylamines, amino sugars, for example those in which the amino group can optionally be substituted by at least one lower alkyl radical, cycloalkylamines, such as mono- or di-cyclo-lower alkylamines, basic amino acids, cyclic amines, such as lower alkyleneamines or lower alkenyleneamines having from 2 to 6 carbon atoms, it being possible for the carbon chain also to be interrupted by aza, N-lower alkylaza, oxa and/or thia. Mono-, di- or tri-lower alkylamines are, for example, ethylamine or tert.-butylamine, diethylamine or diisopropylamine, trimethylamine or triethylamine, and lower alkylenediamine is, for example, ethylenediamine. As phenyl-lower alkylamines there come into consideration, for example, benzylamine or 1- or 2-phenylethylamine. Mono-, di- or tri-hydroxy-lower alkylamines are, for example, mono-, di-, tri-ethanolamine or diisopropanolamine; an oligohydroxy-lower alkylamine is, for example, tris-(hydroxymethyl)-methylamine; and hydroxy-lower alkyl-di-lower alkylamines are, for example, N,N-dimethylamino- or N,N-diethylamino-ethanol. Amino sugars are derived, for example, from monosaccharides in which an alcoholic hydroxy group is replaced by an amino group, such as D-glucosamine, D-galactosamine or marmosamine. N-methyl-D-glucosamine may be mentioned as an example of an N-lower alkylated amino sugar. Mono- or di-cyclo-lower alkylamine is, for example, cyclohexylamine or dicyclohexylamine. Basic amino acids are, for example, arginine, histidine, lysine or ornithine. Lower alkyleneamines and lower alkenyleneamines are, for example, azirine, pyrrolidine, piperidine or pyrroline and as lower alkyleneamines and lower alkenyleneamines of which the carbon chain is interrupted by aza, N-lower alkylaza, oxa and/or thia there are suitable, for example, imidazoline, 3-methylimidazoline, piperazine, 4-methyl- or 4-ethylpiperazine, morpholine or thiomorpholine.

As non-essential constituents of the base substance according to the invention there may be used, if desired, chemical stabilisers, moisture-retaining agents, if necessary bases for neutralising acidic groups, i.e. groups that yield protons, and/or perfumes.

As chemical stabilisers there come into consideration, for example, anti-oxidants which prevent the oxidative decomposition of active ingredients and adjuncts. Suitable for this purpose are, for example, alkali metal sulphites, such as sodium or potassium sulphite, sodium or potassium bisulphite, alkali metal dithionites, such as sodium or potassium dithionite, or ascorbic acid, and also cysteine, cystine and hydrohalides, such as hydrochlorides, thereof. Suitable as anti-oxidants for fats, oils and emulsions are, for example, ascorbyl palmitate, tocopherols (vitamin E), phenols, for example propyl gallate, butylhydroxyanisole or butylhydroxytoluene. Additional protection against heavy metal anions, chiefly $Cu^{2+}$ ions, is effected by the addition of complex formers, such as citric acid or, above all, ethylenediaminetetraacetic acid and salts thereof, such as alkali metal or alkaline earth metal salts, for example the corresponding disodium or calcium compounds. Preferably, an addition of approximately 0.1% by weight of sodium sulphite is used.

The conditions that must be met by suitable moisture-retaining agents are a high affinity for water, it being necessary that the moisture range be narrow, a high viscosity and good tolerability. In addition, these substances should not have corrosive properties. There come into consideration, above all, polyhydric alcohols having at least two hydroxy functions, such as butanediols, glycerine, sorbitol, mannitol, glucose, ethylene glycol or propylene glycol.

As bases for neutralising acidic groups, i.e. groups yielding protons, there are suitable, for example, those that result in the salts of active ingredients described above. Especially preferred bases are the mentioned organic amines. In addition to the active ingredients, especially gel structure formers having acidic groups are also neutralised. The addition of base serves especially to adjust the pH value. Consequently, the addition of base may be essential.

The process for the manufacture of the pharmaceutical composition according to the invention is characterised in that the gel formed by dispersing the gel structure former in a portion of the water, the solution of the nonsteroidal, anti-inflammatorially active compound having at least one acidic group in the water-soluble, volatile lower alkanol having from 2 up to and including 4 carbon atoms, in the co-solvent and in a portion of the water, and the fatty phase formed by mixing the lipid constituents or, if these are not miscible when cold, by melting them together, are mixed optionally while heating and, if desired, the non-essential constituents are incorporated.

The order of mixing the gel, active ingredient solution, fatty phase and neutralising agent is unimportant in the manufacture of the formulation.

The novel, topically administrable pharmaceutical composition is prepared, for example, as follows:

In a preferred procedure, in a first step the formation of a gel is effected by dispersing a gel structure former in a portion of the water. If the gel structure former has, for example, groups that yield protons, such as carboxy groups, these groups may, if desired, be neutralised with a neutralising agent.

In the second step a solution of the active ingredient in the lower alkanol and a co-solvent and in a portion of the water is produced and is incorporated into the gel. In the next step there takes place, if necessary, the preparation of the fatty phase by mixing the fat constituents or, if these are not miscible when cold, by melting them together, for example while heating to from approximately 50° to approximately 80° C.

In the following step the fatty phase is stirred into the gel, optionally while heating, for example in a boiling water bath. In the last step the non-essential constituents, such as anti-oxidants or perfumes, can optionally be incorporated into the base substance while stirring.

In a variant of the manufacturing process the neutralisation of the gel structure former and of the active ingredient, if they contain groups that yield protons, and also for the purpose of setting the desired pH value can be effected after stirring the fatty phase into the gel.

A modification of the described procedure comprises, for example, after swelling the gel structure former in water, after optional neutralisation of the same and/or adjustment of the pH value by means of a neutralising agent, first of all stirring the fatty phase into the gel and then incorporating the active ingredient solution and, if desired, the non-essential constituents.

In a further variant for the formation of the novel formulation, to form the gel, the gel structure former is allowed to swell in a portion of the water, the active ingredient solution is stirred in, neutralised if desired, and then an emulsifier is added to the aqueous phase. Subsequently, the fatty phase and, if desired, the non-essential constituents are stirred in.

The invention relates also to the formulations and their manufacturing processes described in the Examples.

The following Examples illustrate the invention described above but they are not intended to limit the scope thereof in any way. Temperatures are given in degrees Centigrade.

EXAMPLE 1

A pharmaceutical formulation for topical administration, containing diethylammonium 2-(2,6-dichloroanilino)-phenyl acetate, is manufactured as follows:

Composition

| Composition | |
|---|---|
| active ingredient | 1.16% by weight |
| isopropanol | 20.0% by weight |
| diethylamine | 0.7% by weight |
| acrylic acid polymerisate (Carbopol 934 P) | 1.0% by weight |
| sodium sulphite | 0.1% by weight |
| polyhydroxyethylene cetyl stearyl ether (Cetomacrogol 1000) | 2.0% by weight |
| paraffin oil, viscous | 2.5% by weight |
| caprylic/capric acid ester (Cetiol LC) | 2.5% by weight |
| polyethylene glycol 300 | 3.0% by weight |
| water, demineralised to make up to | 100.0% by weight |

The acrylic acid polymerisate (Carbopol 934 P) is dispersed in a portion of the water by means of a rotor-stator homogeniser (for example Homorex). A solution of active ingredient, diethylamine, sodium sulphite and polyethylene glycol 300 in isopropanol and the remaining water is added thereto and distributed homogeneously.

To form the fatty phase, the polyhydroxyethylene cetyl stearyl ether (Cetomacrogol 1000), caprylic/capric acid ester (Cetiol LC) and the paraffin oil are melted together at 75°, slowly added to the previously formed gel and emulsified.

EXAMPLE 2

A pharmaceutical formulation for topical administration, containing diethylammonium 2-(2,6-dichloroanilino)-phenyl acetate, is manufactured as follows:

Composition

| Composition | |
|---|---|
| active ingredient | 1.16% by weight |
| isopropanol | 20.0% by weight |
| diethylamine | 0.7% by weight |
| 1,2-propylene glycol | 10.0% by weight |
| acrylic acid polymerisate (Carbopol 934 P) | 1.2% by weight |
| polyhydroxyethylene cetyl stearyl ether (Cetomacrogol 1000) | 0.9% by weight |
| paraffin oil, viscous | 2.0% by weight |
| caprylic/capric acid ester (Cetiol LC) | 2.5% by weight |
| water, demineralised to make up to | 100.0% by weight |

The acrylic acid polymerisate (Carbopol 934 P) is dispersed in a portion of the water by means of a Homorex. The slime formed is added to the solution of the active ingredient in propylene glycol, isopropanol and a further portion of the water. The fatty phase, consisting of the paraffin oil, polyhydroxyethylene cetyl stearyl ether (Cetomacrogol 1000) and caprylic/capric acid ester (Cetiol LC), which is formed by melting the constituents together at approximately 70°, is incorporated into the gel while stirring and mixing. The diethylamine is then dissolved in the remaining water, the solution is added to the formulation and the whole is stirred for a further 30 minutes and deaerated.

EXAMPLE 3

In a manner analogous to that described in Example 1, a pharmaceutical formulation for topical administration, containing triethanolammonium 2-(2,6-dichloroanilino)-phenyl acetate, is obtained.

Composition

| Composition | |
|---|---|
| active ingredient | 1.4% by weight |
| isopropanol | 20.0% by weight |
| triethanolamine | 2.0% by weight |
| acrylic acid polymerisate (Carbopol 934 P) | 1.0% by weight |
| sodium sulphite | 0.1% by weight |
| polyhydroxyethylene cetyl stearyl ether (Cetomacrogol 1000) | 2.0% by weight |
| paraffin oil, viscous | 2.5% by weight |
| caprylic/capric acid ester (Cetiol LC) | 2.5% by weight |
| polyethylene glycol 300 | 3.0% by weight |
| water, demineralised to make up to | 100.0% by weight |

EXAMPLE 4

A pharmaceutical formulation with diethanolammonium 2-(2,6-dichloroanilino)-phenyl acetate as active ingredient is obtained in a manner analogous to that described in Example 1 in the following composition:

| active ingredient | 1.26% by weight |
|---|---|
| isopropanol | 20.0% by weight |
| diethanolamine | 1.2% by weight |
| acrylic acid polymerisate (Carbopol 934 P) | 1.0% by weight |
| sodium sulphite | 0.1% by weight |
| polyhydroxyethylene cetyl stearyl ether (Cetomacrogol 1000) | 2.0% by weight |
| paraffin oil, viscous | 2.5% by weight |
| caprylic/capric acid ester (Cetiol LC) | 2.5% by weight |
| polyethylene glycol 300 | 3.0% by weight |
| water, demineralised to make up to | 100.0% by weight |

EXAMPLE 5

In a manner analogous to that described in either one of Examples 1 and 2, a pharmaceutical formulation having diethanolammonium 2-[3-chloro-4-(3-pyrrolin-1-yl)-phenyl]-propionate as active ingredient and the following composition is obtained:

| active ingredient | 3.0% by weight |
|---|---|
| diethanolamine | 2.5% by weight |
| acrylic acid polymerisate (Carbopol 934 P) | 2.0% by weight |
| isopropanol | 20.0% by weight |
| polyethylene glycol 300 | 3.0% by weight |
| disodium salt of ethylenediamine-tetraacetic acid | 0.05% by weight |
| polyhydroxyethylene cetyl stearyl ether (Cetomacrogol 1000) | 2.0% by weight |
| paraffin oil, viscous | 2.5% by weight |
| caprylic/capric acid ester (Cetiol LC) | 2.5% by weight |
| water, demineralised to make up to | 100.0% by weight |

EXAMPLE 6

In a manner analogous to that described in either one of Examples 1 and 2, a pharmaceutical formulation containing the active ingredient 2-(6-methoxy-2-naphthyl)-propionic acid or 1-(p-chlorobenzoyl)-5-methoxy-2-methyl-indole-3-acetic acid and having the following composition is obtained:

| active ingredient | 3.0% by weight |
|---|---|
| acrylic acid polymerisate (Carbopol 934 P) | 1.0% by weight |
| triethanolamine | 4.0% by weight |
| isopropanol | 20.0% by weight |
| Carbowax 1500 | 3.0% by weight |
| paraffin oil, viscous | 2.5% by weight |
| isopropyl myristate | 2.5% by weight |
| polyoxyethylene glycerine monostearate (Tagat S) | 2.0% by weight |
| water, demineralised to make up to | 100.0% by weight |

EXAMPLE 7

In a manner analogous to that described in either one of Examples 1 and 2, a pharmaceutical formulation containing 2-[3-chloro-4-(3-pyrrolin-1-yl)-phenyl]-propionic acid or the corresponding triethanolammonium salt as active ingredient and having the following composition is obtained:

| active ingredient | 3.0% by weight |
|---|---|
| triethanolamine | 4.0% by weight |
| acrylic acid polymerisate (Carbopol 934 P) | 2.0% by weight |
| isopropanol | 20.0% by weight |
| polyethylene glycol 300 | 3.0% by weight |
| disodium salt of ethylenediamine-tetraacetic acid | 0.05% by weight |
| polyhydroxyethylene cetyl stearyl ether (Cetomacrogol 1000) | 2.0% by weight |
| paraffin oil, viscous | 2.5% by weight |
| caprylic/capric acid ester (Cetiol LC) | 2.5% by weight |
| water, demineralised to make up to | 100.0% by weight |

We claim:
1. A topically administrable pharmaceutical composition in the form of an oil/water emulsion and containing, as active ingredient, a non-steroidal, anti-inflammatorily active compound having at least one acidic group, characterized in that said composition has a pH of from approximately 5 to approximately 7.5 and containing:
(a) from approximately 10 to approximately 50% by weight of a water-soluble, volatile lower alkanol having from 2 up to and including 4 carbon atoms,
(b) from approximately 1 to approximately 20% by weight of a polyhydric alcohol or a poly-lower alkylene glycol having a chain length of from approximately 200 to approximately 6000 units as co-solvent,
(c) from approximately 40 to approximately 80% by weight of water,
(d) from approximately 3 to approximately 15% by weight of a liquid, semi-solid or solid hydrocarbon; a fatty alcohol having 1 or 2 hydroxy functions and approximately from 6 to 34 carbon atoms; a fatty acid ester with glycerine, the fatty acid having from 6 to 24 carbon atoms; a fatty acid ester of a lower alcohol, having from 1 up to and including 12 carbon atoms or of a higher even-numbered aliphatic alcohol having from 16 to 36 carbon atoms, the fatty acid having from 6 to 34 carbon atoms; or a fatty alcohol of approximately from 6 to 34 carbon atoms etherified by a lower alkanol or a lower alkoxy-lower alkanol; as a lipid, or a mixture thereof, (e) in the presence or absence of from approximately 0.5 to approximately 5% by weight of a readily or sparingly soluble fatty acid salt; a salt of a fluorinated fatty acid, of an alkoxy-carboxylic acid, of a sulphonamido carboxylic acid, of a fatty acid lactate, or of an alkylmalonic or alkylsuccinic acid; a sparingly soluble alkyl sulphonate; a sulphonated fatty acid alkyl ester; a fatty acid sulphonate; a fatty acid ester sulphonate; a perfluorinated alkyl sulphonate; a readily or sparingly soluble alkylbenzene sulphonate; a sulphated primary or secondary fatty alcohol; a soap, sulphated ester, amide, alkanolamide, mono- or polyglyceride or polyglycol ether, of a fatty alcohol or alkylphenol; a fatty acid ester with a mono- or poly-hydric alcohol; a fatty acid ester with an oligo-hydroxy compound or with a polyhydroxy compound; a polyethylene or polypropylene glycol ether having approximately from 2 to 23 ethylene glycol or ethylene oxide units of a fatty alcohol, of a fatty acid ester or of fatty amines derived from fatty alcohols; ethylene oxide or propylene oxide block copolymers having hydrophilic polyhydroxyethylene groups or hydrophobic polyhydroxypropylene groups having a molecular weight of from approximately 1000 to approximately 11000, the fatty acid each having from 6 to 34 carbon atoms and the fatty alcohol having approximately from 6 to 34 carbon atoms; as emulsifier, and present if the lipid phase is not self-emulsifying, (f) from approximately 0.5 to approximately 2% by weight of a synthetic gel-forming macromolecule, the units of which are vinyl alcohol, vinyl pyrrolidine, acrylic or methacrylic acid as gel structure former, and (g) from approximately 0.1 to approximately 10% by weight of a non-steroidal, anti-inflammatorily active compound having at least one acidic group.

2. Pharmaceutical composition according to claim 1, characterised in that it contains isopropanol as water-soluble, volatile lower alkanol.

3. Pharmaceutical composition according to claim 1, characterised in that the lower alkanol portion constitutes at least 15% by weight of the composition.

4. Pharmaceutical composition according to claim 1, characterised in that the lower alkanol portion constitutes approximately from 20 to 30% by weight of the composition.

5. Pharmaceutical composition according to claim 1, characterised in that it contains, as co-solvent, a polyethylene or propylene glycol.

6. Pharmaceutical composition according to claim 1, characterised in that the content of co-solvent is from, approximately 5 to approximately 10% by weight of the composition.

7. Pharmaceutical composition according to claim 1, characterised in that it contains, as lipid constituent, caprylic/capric acid esters of saturated fatty alcohols having from 12 up to and including 18 carbon atoms.

8. Pharmaceutical composition according to claim 1, characterised in that the content of fatty phase constituent is from approximately 5 to approximately 10% by weight of the composition.

9. Pharmaceutical composition according to claim 1, characterised in that it contains, as emulsifiers, alkali metal salts of fatty alcohol sulphates.

10. Pharmaceutical composition according to claim 1, characterised in that it contains, as gel structure former, a polyacrylate.

11. Pharmaceutical composition according to claim 1, characterised in that the content of gel structure former is from approximately 0.5 to approximately 1.5% by weight of the composition.

12. Pharmaceutical composition according to claim 1, characterised in that it contains, as non-steroidal, anti-inflammatorily active compound having at least one acidic group, a phenyl-lower alkanecarboxylic acid or a salt thereof.

13. Pharmaceutical composition according to claim 1, characterised in that it contains, as non-steroidal, anti-inflammatorily active compound having at least one acidic group, diclofenac or a salt thereof.

14. Pharmaceutical composition according to claim 1, characterised in that the content of non-steroidal, anti-inflammatorily active compound is from approximately 1 to approximately 5% by weight of the composition.

15. Pharmaceutical composition according to claim 1, characterised in that it also contains, as non-essential constituents, chemical stabilisers, moisture-retaining agents, bases for neutralising groups that yield protons, and/or perfumes.

16. Method for the treatment of painful conditions, inflammation and/or rheumatic diseases comprising administering topically to a warm-blooded animal an effective amount of a pharmaceutical composition according to claim 1.

17. The composition of claim 1 wherein said water-soluble, volatile lower alkanol is ethanol.

18. The composition of claim 1 wherein said polyhydric alcohol or poly-lower alkylene glycol is a polyhydric alcohol selected from glycerine, ethylene glycol, and propylene glycol.

19. The composition of claim 13 wherein said salt of diclorfenac is selected from the sodium, the ammonium, and the diethylammonium salts of diclofenac.

20. The composition of claim 1 wherein said pH is approximately 7.5.

21. The composition of claim 19 wherein said water-soluble, volatile lower alkanol is ethanol; said polyhydric alcohol or poly-lower alkylene glycol is a polyhydric alcohol selected from glycerine, ethylene glycol, and propylene glycol; and said pH is approximately 7.5.

* * * * *